US012673929B2

(12) United States Patent
Luo et al.

(10) Patent No.: US 12,673,929 B2
(45) Date of Patent: Jul. 7, 2026

(54) PREPARATION METHOD FOR CANNFLAVIN COMPOUNDS

(71) Applicant: DEYI PHARMACEUTICAL LTD., Kunming (CN)

(72) Inventors: Junlu Luo, Kunming (CN); Hongtao Mou, Kunming (CN); Yesong Du, Kunming (CN); Xin Tan, Kunming (CN); Shubin Wang, Kunming (CN); Pingping Zhang, Kunming (CN); Lan Lan, Kunming (CN)

(73) Assignee: DEYI PHARMACEUTICAL LTD., Yunnan (CN)

( * ) Notice: Subject to any disclaimer, the term of this patent is extended or adjusted under 35 U.S.C. 154(b) by 509 days.

(21) Appl. No.: 18/036,140

(22) PCT Filed: Jan. 21, 2021

(86) PCT No.: PCT/CN2021/073144

§ 371 (c)(1),
(2) Date: May 9, 2023

(87) PCT Pub. No.: WO2022/099930

PCT Pub. Date: May 19, 2022

(65) Prior Publication Data

US 2024/0018114 A1 Jan. 18, 2024

(30) Foreign Application Priority Data

Nov. 12, 2020 (CN) ........................ 202011261866.X

(51) Int. Cl.
*C07D 311/30* (2006.01)

(52) U.S. Cl.
CPC .................................. *C07D 311/30* (2013.01)

(58) Field of Classification Search
CPC ............................ C07D 311/30; C07D 311/40
See application file for complete search history.

(56) References Cited

U.S. PATENT DOCUMENTS 9,090,583 B2 * 7/2015 Ding ....................... A61P 35/02

FOREIGN PATENT DOCUMENTS

| | | | | |
|---|---|---|---|---|
| CN | 102018698 | A | | 4/2011 |
| CN | 102558164 | A | | 7/2012 |
| CN | 104031016 | A | * | 9/2014 |
| CN | 107686472 | A | * | 2/2018 |
| CN | 109369591 | A | | 2/2019 |
| WO | 2017027136 | A2 | | 2/2017 |
| WO | 2017/091837 | A2 | | 6/2017 |

OTHER PUBLICATIONS

Thevenin (Eur. J. Org. Chem. 2018, 5843-5852).*
Raikar (Eur. J. Org. Chem. 2008, 1358-1369).*
Erridge (Fitoterapia 146 (2020) 104712).*
International Search Report for PCT/CN2021/073145 mailed Aug. 18, 2021, 3 pages.
Written Opinion of the ISA for PCT/CN2021/073145 mailed Aug. 18, 2021, 4 pages.

* cited by examiner

*Primary Examiner* — Valerie Rodriguez-Garcia
(74) *Attorney, Agent, or Firm* — NIXON & VANDERHYE, PC

(57) ABSTRACT

Disclosed is a preparation method for cannflavin compounds. The preparation method has the advantages of cheap and easily available raw materials, few reaction steps, short production period, simple operation, etc. The method comprises: firstly, condensing 4'-hydroxy-3'-methoxyacetophenone and diethyl carbonate (DEC) under an alkaline condition to obtain 4'-hydroxy-3'-methoxybenzoyl acetate; reacting 1,3,5-trihydroxybenzene with bromo-isoamylene under an alkaline condition to obtain 2-isopentenyl-1,3,5-trihydroxybenzene; and finally, condensing 4'-hydroxy-3'-methoxybenzoyl acetate and 2-isopentenyl-1,3,5-trihydroxybenzene at a high temperature to produce cannflavin B and/or isocannflavin B, and then subjecting same to separation and purification to obtain pure cannflavin B and pure isocannflavin B.

10 Claims, No Drawings

PREPARATION METHOD FOR CANNFLAVIN COMPOUNDS

CROSS-REFERENCE TO RELATED APPLICATIONS

This application is the U.S. national phase of International Application No. PCT/CN2021/073144 filed Jan. 21, 2021, which designated the U.S. and claims priority to CN 202011261866.X filed Nov. 12, 2020.

TECHNICAL FIELD

The present invention relates to the field of chemical synthesis, and particularly to a preparation method for a cannflavin compound, especially cannflavin B and/or isocannflavin B.

BACKGROUND

Among over 200 biologically-active compounds of *Cannabis sativa*, cannabinoids and terpenes have been of greatest concern. However, there is another important compound in *Cannabis sativa*, that is cannflavin compounds which account for 10% of these known compounds, of which about 20 types are known to be present in *Cannabis sativa*, and these flavonoids have no psychoactive properties. It has been studied that cannflavin B has an anti-inflammatory effect as early as in 1985, which is nearly 30 times higher than that of acetylsalicylic acid (sold as aspirin). In contrast to other analgesic agents, this ingredient does not induce a risk of drug dependence and addiction in patients.

Moreau et al. reported in Flavonoid Derivative of *Cannabis* Demonstrates Therapeutic Potential in Preclinical Models of Metastatic Pancreatic Cancer. (W. Front. Oncol, 2019, 9:660) that researchers extracted a neoflavonoid compound, that is caflanone or FBL-03G or isocannflavin B, which is an isomer of cannflavin B, with cannflavin B found from local *Cannabis sativa* L. strain in Jamaica with chromatography. The researchers performed in vitro and in vivo experiments successively. In vivo experiment results showed therapeutic effects of delaying local and metastatic tumor progression in pancreatic cancer animal models when 1-BL-03G was provided continuously by using smart radiotherapy biomaterials. Compared with the control group, repeated tests also showed a significant increase in survival of pancreatic cancer animals. Research results showed that the isoform of cannabinoid B (caflanone or 1-BL-03G or isocannflavin B) has important therapeutic potential for the treatment of pancreatic cancer, including therapeutic potential for radiosensitization and tumor metastasis. These results provide the basis for further study and optimization of the therapeutic results in clinical trials. The isoform of cannabinoid B (caflanone or FBL-03G or isocannflavin B) was approved by FDA as an orphan drug in September 2019, and is expected to enter clinical research in this year.

The content of flavonoids in *Cannabis sativa* plants is much less than 1%, less than 0.14% on average, the content of cannflavin B in *Cannabis sativa* is extremely low, and the content of Caflanone or FBL-03G or isocannflavin B is much lower. Therefore, it is infeasible to rely solely on *Cannabis sativa* plant extraction to obtain these components. Currently, researchers are working on the preparation of these active factors based on biological systems, which will create a great deal of opportunities for cannflavins.

Rea et al. reported in Biosynthesis of cannflavins A and B from *Cannabis sativa* L. ([0.1]. Phytochemistry, 2019, 134, 162-171) the synthesis of cannabinoid B from dimethylallyl diphosphate under the catalysis of aromatic prenyltransferase of *Sinorhizobium meliloti*. However, this biosynthesis method is costly and not easily scalable industrially.

Patent document WO2017091837 discloses a method as follows: synthesizing a main chain of cannflavin compounds by using a known chemical synthesis technology with 2,4,6-trihydroxyacetophenone as a starting reactant, then forming a tricyclic structure by conjugating and ring closing, and finally performing a series of enzymatic modifications to obtain cannflavin B and flavonoid compounds.

Minassi et al. reported in A Regiodivergent Synthesis of Ring A C-Prenylflavones. ([J]. Org. Lett., 2008, 10(11), 2267-2270) the regioselective synthesis of cannflavin B and/or isocannflavin B from isoprenylated dimethylsilyl benzophenone under a mild condition using a protecting group strategy and a modified Robinson flavone synthesis method.

Li Wei et al. reported in Regioselective synthesis of C-prenylated flavonoids via intramolecular [1,3] or [1,5] shift reaction catalyzed by acidic clays. (W. Tetrahedron Letters, 2019, 60, 151138) the efficient and regioselective synthesis of cannflavin B and/or isocannflavin B using diosmetin or quercetin as a starting reactant via intramolecular [1,3] or [1,5] shift reaction of isopentenyl flavonoids catalyzed by Florisil or montmorillonite K10.

The chemical synthesis methods disclosed have the defects of long synthesis steps, multi-step reactions requiring silica gel column chromatography for purification, and difficulty in amplification. Therefore, there is an urgent need for a novel method for synthesizing cannflavin B and/or isocannflavin B, which is simple, rapid, and easily scale-up.

SUMMARY

The present invention provides a preparation method for a cannflavin compound. The preparation method has the advantages of cheap and easily available raw materials, few reaction steps, short production period, simple operation, etc.

The present invention aims to provide a preparation method for a cannflavin compound, which comprises the following steps:

condensing

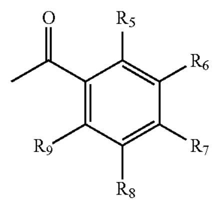

and diethyl carbonate under an alkaline condition to obtain

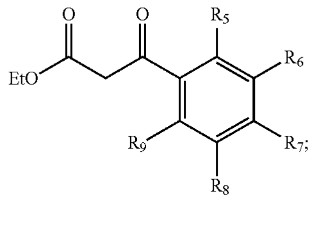

reacting

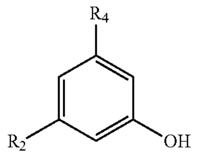

with a halide ($R_3$—X) under an alkaline condition to obtain

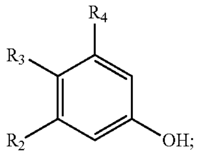

and reacting

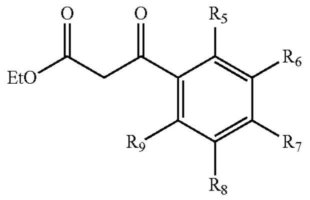

with

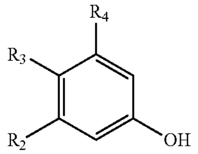

to obtain the cannflavin compound;

wherein the cannflavin compound has a structure of general formula I:

I

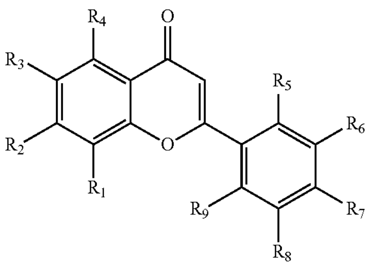

$R_5$, $R_6$, $R_7$, $R_8$ and $R_9$ are independently selected from the group consisting of: H, $C_{1-14}$ alkyl, $C_{3-14}$ alkenyl, hydroxy, $C_{1-5}$ alkoxy, carboxyl, amino and halogen;

$R_2$ and $R_4$ are independently selected from the group consisting of: H, $C_{1-14}$ alkyl, $C_{3-14}$ alkenyl, hydroxy, $C_{1-5}$ alkoxy, carboxyl and halogen; and $R_3$ and $R_1$ are independently selected from the group consisting of: H, $C_{1-14}$ alkyl, $C_{3-14}$ alkenyl and $C_{1-5}$ alkoxy.

Preferably, $R_2$ is hydroxy; preferably, $R_4$ is hydroxy; preferably, $R_7$ is hydroxy; preferably, $R_6$ is methoxy; preferably, $R_3$ is isopentenyl; preferably, $R_5$ is H; preferably, $R_8$ is H; preferably, $R_9$ is H; and preferably, $R_1$ is isopentenyl.

Furthermore, the preparation method comprises the following steps:

condensing

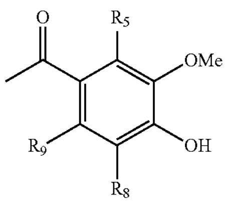

and diethyl carbonate under an alkaline condition to obtain

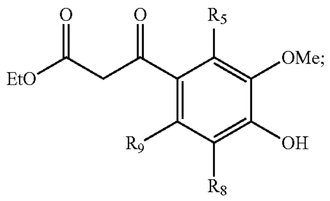

reacting

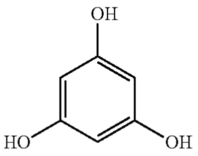

with a halide ($R_3$—X) under an alkaline condition to obtain

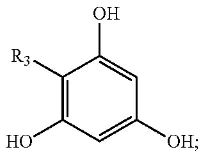

and reacting

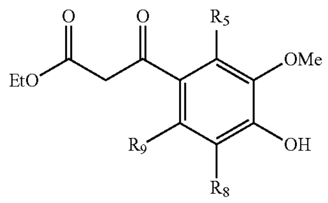

with

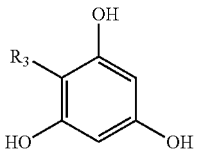

to obtain the cannflavin compound;

wherein the cannflavin compound has a structure of general formula II:

II

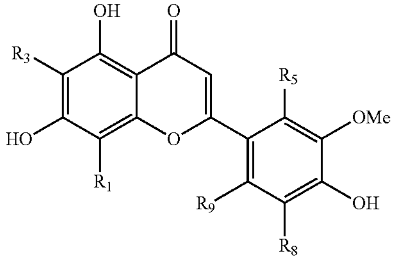

$R_5$, $R_8$ and $R_9$ are independently selected from the group consisting of: H, $C_{1-14}$ alkyl, $C_{3-14}$ alkenyl, hydroxy, $C_{1-5}$ alkoxy, carboxyl, amino and halogen; and $R_3$ and $R_1$ are selected from the group consisting of: H, $C_{1-14}$ alkyl, $C_{3-14}$ alkenyl and $C_{1-5}$ alkoxy.

Preferably, $R_3$ is isopentenyl; preferably, $R_5$ is H; preferably, $R_8$ is H; preferably, $R_9$ is H; and preferably, $R_1$ is isopentenyl.

The present invention also aims to provide a method for preparing cannflavin B and/or isocannflavin B with 1,3,5-trihydroxybenzene and 4'-hydroxy-3'-methoxyacetophenone as starting materials, which comprises the following steps:

step (1): condensing 4'-hydroxy-3'-methoxyacetophenone and diethyl carbonate under an alkaline condition to obtain ethyl 4'-hydroxy-3'-methoxybenzoylacetate;

step (2): subjecting 1,3,5-trihydroxybenzene and bromo-isoamylene to a C-alkylation reaction under an alkaline condition to obtain 2-isopentenyl-1,3,5-trihydroxybenzene; and step (3): condensing ethyl 4'-hydroxy-3'-methoxybenzoylacetate obtained in the step (1) and 2-isopentenyl-1,3,5-trihydroxybenzene obtained in the step (2) at a high temperature to produce cannflavin B and/or isocannflavin B, followed by separation and purification to obtain pure cannflavin B and isocannflavin B.

The reaction equation of the step (2) is as follows:

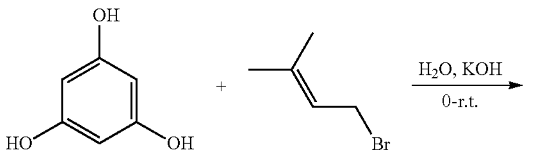

-continued

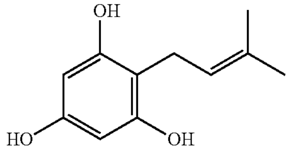

Preferably, in the step (2), the reaction is performed under an alkaline condition, and more preferably, the alkaline condition is that an alkali, such as an inorganic alkali, is included in the reaction system, and the inorganic alkali is one or a mixture of more selected from the group consisting of: pure inorganic alkali of potassium hydroxide and an aqueous solution thereof; and in one embodiment of the present invention, the inorganic alkali is potassium hydroxide.

More preferably, the mass-molar ratio of the alkali to bromo-isoamylene is 50-1000 g/mol, and further preferably, 100-150 g/mol, and further preferably, the mass-molar ratio of the alkali to bromo-isoamylene is 100 g/mol, 110 g/mol, 120 g/mol, 130 g/mol, 140 g/mol or 150 g/mol. Preferably, in the step (2), the reaction system further comprises a solvent selected from the group consisting of: water and/or methanol; and in one embodiment of the present invention, the solvent is water.

Preferably, in the step (2), the molar ratio of 1,3,5-trihydroxybenzene to bromo-isoamylene is 1:1 to 3:1, and further preferably, the molar ratio of 1,3,5-trihydroxybenzene to bromo-isoamylene is 1:1, 1.9:1, 2:1 or 3:1, and most preferably, 1.9:1.

Preferably, in the step (2), the reaction temperature is 0-25° C., and further preferably, the reaction temperature is 0° C., 5° C., 10° C., 15° C., 20° C. or 25° C.

Preferably, in the step (2), the reaction time is 8-24 h, and further preferably, the reaction time is 8 h, 12 h, 16 h, 20 h or 24 h, and most preferably, 12 h.

Preferably, in the step (2), bromo-isoamylene is added dropwise to 1,3,5-trihydroxybenzene.

In one embodiment of the present invention, the step (2) comprises the following specific steps: adding water and potassium hydroxide into a reaction vessel, stirring, then adding 1,3,5-trihydroxybenzene, cooling, adding dropwise bromo-isoamylene, stirring, reacting and then performing post-treatment on the resulting reaction liquid to obtain 2-isopentenyl-1,3,5-trihydroxybenzene.

Preferably, the post-treatment comprises a quenching step.

More preferably, the quenching comprises the following specific steps: adding a quenching solvent to the reaction vessel, and adding an acid to adjust pH of the mixture to 4.0-7.0.

More preferably, the quenching solvent is one or more selected from the group consisting of: methyl tert-butyl ether, diethyl ether, ethyl acetate and butyl acetate; and in one embodiment of the present invention, the quenching solvent is ethyl acetate.

More preferably, the acid is an inorganic acid, which is one or a mixture of more selected from the group consisting of: pure inorganic acid of hydrochloric acid and an aqueous solution thereof; and in one embodiment of the present invention, the acid is hydrochloric acid.

Preferably, the post-treatment further comprises an extraction step after the quenching step.

More preferably, the extraction solvent is one or more selected from the group consisting of: methyl tert-butyl ether, diethyl ether, ethyl acetate and butyl acetate; and in one embodiment of the present invention, the extraction solvent is ethyl acetate.

More preferably, the extraction temperature is 5-40° C., and further preferably, 15-25° C.

In one embodiment of the present invention, the extraction step comprises the following specific steps: adding an extraction solvent to the reaction liquid, and layering; adding an extraction solvent to the aqueous layer for extraction, and layering; combining the organic layers, washing, layering, and then combining the organic layers.

Preferably, the post-treatment further comprises a distillation step after the extraction step; and more preferably, the distillation step comprises atmospheric distillation and vacuum distillation steps.

Preferably, the vacuum distillation temperature is 20-50° C., and the vacuum degree is −0.1 MPa to −0.05 MPa.

Preferably, the post-treatment further comprises a column chromatography step in sequence after the distillation step; and more preferably, the column chromatography step comprises normal-phase column chromatography and reverse-phase column chromatography.

More preferably, the column chromatography is normal-phase column chromatography, and the eluent in the column chromatography is selected from the group consisting of: petroleum ether, n-hexane, ethyl acetate, toluene, triethylamine, dichloromethane, water and methanol; and in one embodiment of the present invention, the eluent is petroleum ether (PE) and ethyl acetate (EA), and the ratio of the eluent is PE:EA=8:1→2:1.

In a preferred embodiment of the present invention, the post-treatment comprises: quenching, extraction, distillation and column chromatography in sequence, wherein the specific operations and conditions of each step are as described above in the present invention.

In one embodiment of the present invention, the preparation method for 2-isopentenyl-1,3,5-trihydroxybenzene comprises the following steps:

(2-1) reaction step: adding water and potassium hydroxide into a reaction vessel, stirring, adding 1,3,5-trihydroxybenzene, cooling, adding dropwise bromo-isoamylene, raising the temperature to room temperature, and reacting for 8-24 h;

(2-2) control step: adding ethyl acetate into the mixture of (2-1), adding hydrochloric acid to adjust pH to 4.0-7.0, and layering; adding ethyl acetate to the aqueous layer for extraction, and layering; combining the organic layers, washing the combined layer with saturated brine, and layering; combining the organic layers, drying the combined layer over anhydrous sodium sulfate, filtering under vacuum, and concentrating the filtrate; and (2-3): separating the concentrate of the step (2-2) by column chromatography (silica gel 200-300 mesh, PE:EA=8:1→2:1) to obtain 2-isopentenyl-1,3,5-trihydroxybenzene as an orange oily substance.

The reaction equation of the step (3) is as follows:

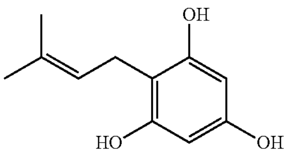

+

-continued

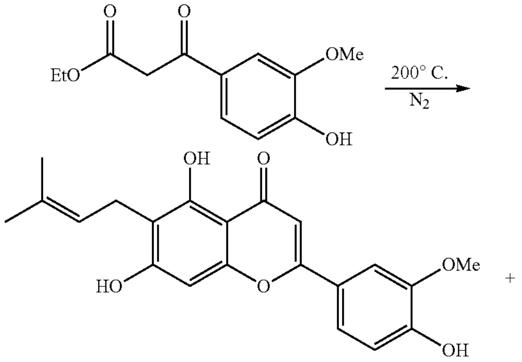

Cannflavin B

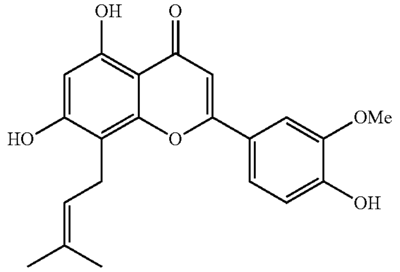

Isocannflavin B

Preferably, in the step (3), the reaction environment is an oxygen-free environment; more preferably, the reaction environment is an inert gas protected reaction environment; and in one embodiment of the present invention, the reaction environment is a nitrogen protected reaction environment.

Preferably, in the step (3), the reaction temperature is 150-230° C.; further preferably, the reaction temperature is 160° C., 180° C., 200° C. or 220° C.; and in one embodiment of the present invention, the reaction temperature is 200° C.

Preferably, in the step (3), the reaction time is 2-8 h; further preferably, the reaction time is 3 h, 5 h or 7 h; and in one embodiment of the present invention, the reaction time is 3 h.

Preferably, in the step (3), the molar ratio of ethyl 4'-hydroxy-3'-methoxybenzoylacetate to 2-isopentenyl-1,3,5-trihydroxybenzene is 1:2 to 3:1, and further preferably, the molar ratio of ethyl 4'-hydroxy-3'-methoxybenzoylacetate to 2-isopentenyl-1,3,5-trihydroxybenzene is 1:2, 1:1, 1.5:1, 2:1 or 3:1, and most preferably, 1.5:1.

In one embodiment of the present invention, the step (3) comprises the following specific steps: adding ethyl 4'-hydroxy-3'-methoxybenzoylacetate and 2-isopentenyl-1,3,5-trihydroxybenzene into a reaction vessel, stirring, heating, reacting, and then performing post-treatment on the resulting reaction liquid to obtain cannflavin B and/or isocannflavin B.

Preferably, the post-treatment also comprises a column chromatography step; and more preferably, the column chromatography step comprises normal-phase column chromatography and reverse-phase column chromatography.

More preferably, the column chromatography step comprises the following steps: subjecting the mixture to normal-phase silica gel column chromatography multiple times followed by reverse-phase silica gel column chromatography multiple times.

More preferably, the eluent in the column chromatography is selected from the group consisting of: petroleum ether, n-hexane, ethyl acetate, toluene, triethylamine, dichloromethane, water and methanol; and in one embodiment of the present invention, the eluent in the normal-phase silica gel column chromatography is petroleum ether (PE) and ethyl acetate (EA), and the ratio of the eluent is PE:EA=10:1→2:1, and the eluent in the reverse-phase silica gel column chromatography is water and methanol, and the ratio of the eluent is water:methanol=8:2→3:7.

Preferably, the post-treatment also comprises a recrystallization step after the column chromatography step; and more preferably, the recrystallization step comprises steps of dissolution and cooling to precipitate.

More preferably, the solvent for dissolution is one or a mixture of more selected from the group consisting of: toluene, methanol, acetone, water, etc.; and in one embodiment of the present invention, the solvent is methanol.

More preferably, the dissolution temperature is 40-100° C., and further preferably, 60-100° C.; and in one embodiment of the present invention, the dissolution temperature is 65° C.

More preferably, the step of cooling to precipitate comprises cooling to 1-30° C.; and in one embodiment of the present invention, the step of cooling to precipitate comprises cooling to 18-22° C.

In one embodiment of the present invention, the recrystallization step comprises the following steps: adding a solvent, heating to 40-100° C., dissolving the solid completely, cooling to 1-30° C., precipitating, and filtering the precipitate.

Preferably, the post-treatment also comprises a drying step after the recrystallization step.

More preferably, the drying step is vacuum drying; and further preferably, the vacuum degree is −0.08 MPa to −0.01 MPa.

More preferably, the drying temperature is 45-65° C.

In a preferred embodiment of the present invention, the post-treatment comprises: column chromatography, recrystallization and drying in sequence, wherein the specific operations and conditions of each step are as described above in the present invention.

In one specific embodiment of the present invention, the preparation method for cannflavin B and/or isocannflavin B comprises the following steps:

(3-1) reaction step: under nitrogen protection, adding ethyl 4'-hydroxy-3'-methoxybenzoylacetate and 2-isopentenyl-1,3,5-trihydroxybenzene into a reaction vessel, stirring, heating to 150-230° C., and reacting for 2-8 h;

(3-2): cooling to room temperature, subjecting the mixture to normal-phase silica gel column chromatography multiple times, followed by reverse-phase silica gel column chromatography multiple times, and evaporating the product to dryness;

(3-3): adding methanol into the evaporated product obtained in the step (3-2), heating to 65° C., dissolving the solid completely, cooling to 18-22° C., precipitating the solid, filtering, and rinsing the filter cake; and (3-4): drying the filter cake obtained in the step (3-3) under vacuum at 50-55° C.

The reaction equation of the step (1) is as follows:

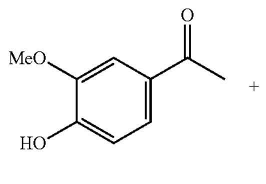

-continued

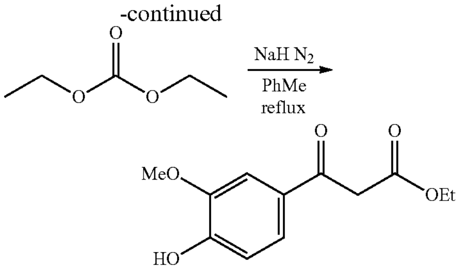

Preferably, in the step (1), the reaction is performed under an alkaline condition, more preferably, the alkaline condition is that an alkali, such as an inorganic alkali, is included in the reaction system, and the inorganic alkali is one or a mixture of more selected from the group consisting of: pure inorganic alkali of sodium hydride and paraffin oil-coated sodium hydride; and in one embodiment of the present invention, the inorganic alkali is paraffin oil-coated sodium hydride.

More preferably, the mass molar ratio of the alkali to 4'-hydroxy-3'-methoxyacetophenone is g/mol, and further preferably, 100-150 g/mol; further preferably, the mass molar ratio of the alkali to 4'-hydroxy-3'-methoxyacetophenone is 100 g/mol, 110 g/mol, 120 g/mol, 130 g/mol, 140 g/mol or 150 g/mol.

Preferably, in the step (1), the reaction system further comprises a solvent selected from the group consisting of: toluene and/or benzene: and in one embodiment of the present invention, the solvent is toluene.

Preferably, in the step (1), the molar ratio of 4'-hydroxy-3'-methoxyacetophenone to diethyl carbonate is 1:3 to 3:1, and further preferably, the molar ratio of 4'-hydroxy-3'-methoxyacetophenone to diethyl carbonate is 1:3, 1:2, 1:1, 1.5:1, 2:1 or 3:1, and most preferably, 1:2.

Preferably, in the step (1), the reaction environment is an oxygen-free environment; more preferably, the reaction environment is an inert gas protected reaction environment; and in one embodiment of the present invention, the reaction environment is a nitrogen protected reaction environment.

Preferably, in the step (1), the reaction temperature is 80-130° C., and further preferably, the reaction temperature is 80° C., 90° C., 100° C., 110° C., 120° C. or 130° C.

Preferably, in the step (1), the reaction time is 2-12 h, further preferably, the reaction time is 4 h, 6 h, 8 h, 10 h or 12 h, and most preferably, 4 h.

Preferably, in the step (1), 4'-hydroxy-3'-methoxyacetophenone is added dropwise to diethyl carbonate.

In one embodiment of the present invention, the step (1) comprises the following specific steps: under nitrogen protection, adding 60% NaH and toluene into a reaction vessel, stirring, then adding diethyl carbonate, heating, adding dropwise a mixture of 4'-hydroxy-3'-methoxyacetophenone and toluene, stirring, reacting, and then performing post-treatment on the resulting reaction liquid to obtain ethyl 4'-hydroxy-3'-methoxybenzoylacetate.

Preferably, the post-treatment comprises a quenching step.

More preferably, the quenching step comprises the following specific step: adding an acid to the reaction vessel to adjust pH of the mixture to 4.0-7.0.

More preferably, the acid is an inorganic acid, which is one or a mixture of more selected from the group consisting of: pure inorganic acid of acetic acid and an aqueous solution thereof; and in one embodiment of the present invention, the acid is acetic acid.

Preferably, the post-treatment also comprises an extraction step after the quenching step.

More preferably, the extraction solvent is one or more selected from the group consisting of: methyl tert-butyl ether, diethyl ether, ethyl acetate and butyl acetate; and in one embodiment of the present invention, the extraction solvent is ethyl acetate.

More preferably, the extraction temperature is 5-40° C., and further preferably, 15-25° C.

In one embodiment of the present invention, the extraction step comprises the following specific steps: adding an extraction solvent into the reaction liquid, and layering; adding an extraction solvent to the aqueous layer for extraction, and layering; combining the organic layers, washing, layering, and then combining the organic layers.

Preferably, the post-treatment further comprises a distillation step after the extraction step; and more preferably, the distillation step comprises atmospheric distillation and vacuum distillation steps.

Preferably, the vacuum distillation temperature is 20-50° C., and the vacuum degree is −0.1 MPa to −0.05 MPa.

Preferably, the post-treatment further comprises washing in sequence after the distillation step; more preferably, the washing solvent is selected from the group consisting of: n-hexane and/or diethyl ether; and in one embodiment of the present invention, the washing solvent is n-hexane.

In a preferred embodiment of the present invention, the post-treatment comprises: quenching, extraction, distillation and washing in sequence, wherein the specific operation and conditions of each step are as described above in the present invention.

In one embodiment of the present invention, the preparation method for ethyl 4'-hydroxy-3'-methoxybenzoylacetate comprises the following steps:

(1-1) reaction step: under nitrogen atmosphere, adding 60% NaH and toluene into a reaction vessel, stirring, then adding diethyl carbonate, heating to 80-130° C., adding dropwise a mixture of 4'-hydroxy-3'-methoxyacetophenone and toluene, stirring, and reacting for 2-12 h;

(1-2) control step: adding acetic acid to the mixture of (1-1) to adjust pH to 4.0-7.0, adding ethyl acetate, and layering; adding ethyl acetate to the aqueous layer for extraction, and layering; combining the organic layers, washing the combined layer with saturated ammonium chloride aqueous solution and saturated brine, and layering; combining the organic layers, drying the combined layer over anhydrous sodium sulfate, filtering under vacuum, and concentrating the filtrate; and (1-3) adding the concentrate obtained in the step (1-2) into n-hexane, stirring for 2-12 h, and filtering to obtain ethyl 4'-hydroxy-3'-methoxybenzoylacetate.

The present invention also provides a preparation method for a cannflavin compound, which comprises the preparation steps of 2-isopentenyl-1,3,5-trihydroxybenzene described above in the present invention.

The present invention also provides use of ethyl 4'-hydroxy-3'-methoxybenzoylacetate in preparing a compound, wherein the compound is cannflavin B and/or isocannflavin B.

Preferably, ethyl 4'-hydroxy-3'-methoxybenzoylacetate is prepared by the following step: condensing 4'-hydroxy-3'-methoxyacetophenone and diethyl carbonate under an alkaline condition to obtain ethyl 4'-hydroxy-3'-methoxybenzoylacetate.

The present invention has the advantages of cheap and easily available raw materials, simple synthetic route, simple operation, short production period, and relatively low synthetic cost, and thus has certain economic value.

DETAILED DESCRIPTION

It should be noted that the detailed description as follows is exemplary and is intended to provide further explanation of the present application. Unless otherwise stated, all technical and scientific terms used herein have the same meaning as that commonly understood by those of ordinary skill in the art to which the present application belongs.

Example 1: Synthesis of Ethyl 4'-hydroxy-3'-methoxybenzoylacetate

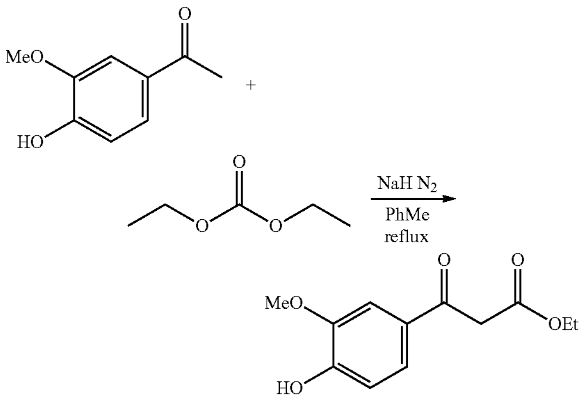

To a reaction flask, 60% NaH (6.00 g, 150 mmol) was added, under nitrogen atmosphere, toluene (60 mL) and DEC (11.82 g, 100 mmol) were added, and the resulting mixture was stirred, and heated to reflux. A solution of 4'-hydroxy-3'-methoxyacetophenone (12.82 g, 50 mmol) in toluene (60 mL) was added dropwise. After the addition was completed, the resulting mixture was refluxed for 4 h, and then cooled to room temperature, adjusted to pH neutral with acetic acid, and added with a saturated ammonium chloride aqueous solution (150 mL). The aqueous phase was extracted with ethyl acetate (100 mL×3). The organic phases were combined, and washed successively with a saturated ammonium chloride aqueous solution (100 mL×2) and saturated brine (100 mL×2). The resulting organic phase was dried over anhydrous sodium sulfate, and filtered under vacuum. The filtrate was concentrated to dryness, added with n-hexane (50 mL), stirred overnight, and filtered to obtain ethyl 4'-hydroxy-3'-methoxybenzoylacetate (15.43 g, 93.9%) as an orange-yellow solid, MS (ESI): 238.9 $[M+H]^+$.

Example 2: Synthesis of 2-isopentenyl-1,3,5-trihydroxybenzene

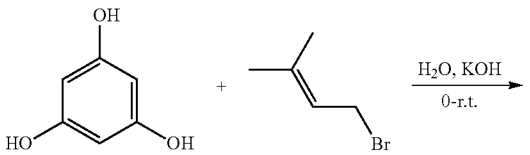

-continued

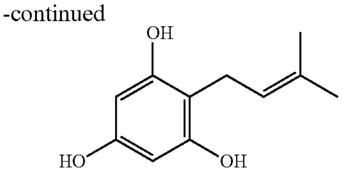

To a reaction flask, water (80 mL) and potassium hydroxide (4.87 g, 73.92 mmol) were added, and the resulting mixture was stirred. 1,3,5-trihydroxybenzene (10.0 g, 79.20 mmol) was added. The resulting mixture was cooled in an ice-water bath, added dropwise with bromo-isoamylene (6.6 g, 41.2 mmol), and stirred overnight. Ethyl acetate (100 mL) was added, and the pH was adjusted to with 1 N hydrochloric acid. The aqueous phase was extracted with ethyl acetate (50 mL×3). The organic phases were combined, washed with saturated brine (100 mL×2), then dried over anhydrous sodium sulfate, and filtered under vacuum. The filtrate was concentrated to dryness, and the resulting oil was separated by column chromatography (silica gel 200-300 mesh, PE:EA=8:1→2:1) to obtain 2-isopentenyl-1,3,5-trihydroxybenzene as an orange oil (3.17 g, 20.6%).

Example 3: Synthesis of Cannflavin B and/or Isocannflavin B

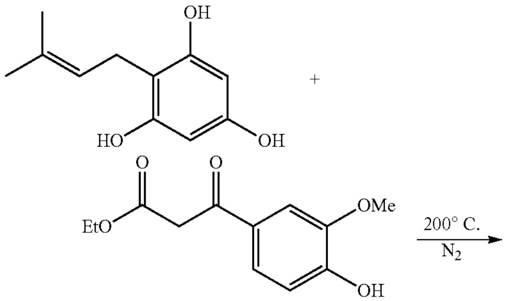

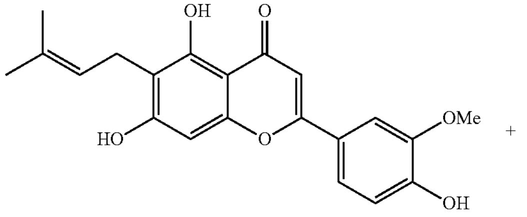

Cannflavin B

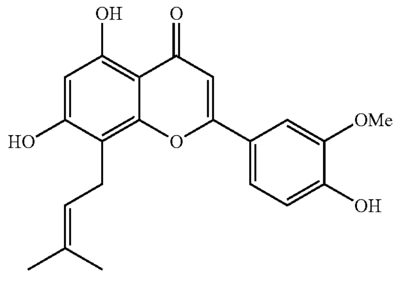

Isocannflavin B

To a reaction flask, ethyl 4'-hydroxy-3'-methoxybenzoylacetate (18.0 g, 75.6 mmol) and 2-isopentenyl-1,3,5-trihydroxybenzene (9.8 g, 50.5 mmol) were added, and the resulting mixture was stirred. The resulting mixture was heated to 200° C. under nitrogen atmosphere, maintained at this temperature for 3 h, and then cooled to room temperature. The resulting product was subjected to normal-phase silica gel column chromatography (silica gel 200-300 mesh, PE:EA=10:1→2:1) multiple times, and then subjected to reverse-phase silica gel column chromatography (reverse-phase silica gel 200-300 mesh, water:methanol=80:20→30:70) multiple times, followed by recrystallization with methanol to obtain cannflavin B as an orange-yellow solid (about 1 g, yield: about 5.4%), and simultaneously obtain isocannflavin B as an orange-yellow solid (about 1 g, yield: about 5.4%).

Cannflavin B: MS (ESI): 369.1 $[M+H]^+$, 1 H NMR (400 MHz, DMSO-$d_6$), δ: 13.22 (s, 1H), 10.83 (s, 1H), 9.95 (s, 1H), 7.56 (d, 1H), 7.54 (s, 1H), 6.92 (d, 1H), 6.89 (s, 1H), 6.55 (s, 1H), 5.18 (t, 1H), 3.89 (s, 3H), 3.21 (d, 2H), 1.72 (s, 3H), 1.62 (s, 3H).

Isocannflavin B: MS (ESI): 369.1 $[M+H]^+$, 1 H NMR (400 MHz, DMSO-$d_6$), δ: 12.89 (s, 1H), 10.76 (s, 1H), 9.98 (s, 1H), 7.53 (s, 1H), 7.52 (d, 1H), 6.93 (d, 1H), 6.86 (s, 1H), 6.28 (s, 1H), 5.22 (t, 1H), 3.87 (s, 3H), 3.42 (d, 2H), 1.74 (s, 3H), 1.62 (s, 3H).

The above descriptions are only preferred examples of the present application and are not intended to limit the present invention, and various modifications and changes may be made by those skilled in the art. Any modifications, equivalent replacements, improvements, and the like that are made within the spirit and principle of the present application shall all fall within the protection scope of the present application.

The invention claimed is:

1. A preparation method for a cannflavin compound, comprising the following steps:

step (1): condensing 4'-hydroxy-3'-methoxyacetophenone and diethyl carbonate under an alkaline condition to obtain ethyl 4'-hydroxy-3'-methoxybenzoylacetate;

step (2): reacting 1,3,5-trihydroxybenzene with bromo-isoamylene under an alkaline condition to obtain 2-isopentenyl-1,3,5-trihydroxybenzene; and step (3): reacting ethyl 4'-hydroxy-3'-methoxybenzoylacetate with 2-isopentenyl-1,3,5-trihydroxybenzene to obtain cannflavin B and/or isocannflavin B;

wherein the step (2) comprises the following steps: adding water and potassium hydroxide into a reaction vessel, stirring, then adding 1,3,5-trihydroxybenzene, cooling, adding dropwise bromo-isoamylene, stirring, reacting, and then performing post-treatment on the resulting reaction liquid to obtain 2-isopentenyl-1,3,5-trihydroxybenzene;

for the step (2): a molar ratio of 1,3,5-trihydroxybenzene to bromo-isoamylene is 1:1 to 2:1;

the reaction temperature is 0-15° C.;

the post-treatment comprises a quenching step, and the quenching step comprises: adding ethyl acetate to the reaction vessel, and adding an acid to adjust pH of the mixture to 4.0-7.0;

the post-treatment further comprises an extraction step after the quenching step, and the extraction step comprises: adding ethyl acetate to the reaction liquid, and layering; adding ethyl acetate to the aqueous layer for extraction, and layering; combining the organic layers, washing, layering, and then combining the organic layers.

2. The preparation method according to claim 1, wherein for the step (1), the reaction is performed under an oxygen-free environment; and the reaction system further comprises a solvent selected from the group consisting of: toluene, benzene, and a combination thereof.

3. The preparation method according to claim 2, wherein the oxygen-free environment in the step (1) is an inert gas protected reaction environment;

the alkali is an inorganic alkali;

a mass molar ratio of the inorganic alkali to 4'-hydroxy-3'-methoxyacetophenone is 50-1000 g/mol;

a molar ratio of 4'-hydroxy-3'-methoxyacetophenone to diethyl carbonate is 1:3 to 3:1;

the reaction temperature is 80-130° C.;

the reaction time is 2-12 h; and

4'-hydroxy-3'-methoxyacetophenone is added dropwise to diethyl carbonate.

4. The preparation method according to claim 1, wherein the step (1) comprises the following steps: under inert gas protection, adding NaH and toluene into a reaction vessel, stirring, adding diethyl carbonate, heating, adding dropwise a mixture of 4'-hydroxy-3'-methoxyacetophenone and toluene, stirring, reacting, and then performing post-treatment on the resulting reaction liquid to obtain ethyl 4'-hydroxy-3'-methoxybenzoylacetate.

5. The preparation method according to claim 1, wherein for the step (2), the reaction system further comprises a solvent selected from the group consisting of: water, methanol, and a combination thereof.

6. The preparation method according to claim 5, wherein in step (2), a mass molar ratio of the potassium hydroxide to bromo-isoamylene is 50-1000 g/mol;

a molar ratio of 1,3,5-trihydroxybenzene to bromo-isoamylene is 1.9:1;

the reaction temperature is 0-10° C.;

the reaction time is 8-24 h.

7. The preparation method according to claim 1, wherein for the step (3), the reaction is performed under an oxygen-free environment.

8. The preparation method according to claim 7, wherein the oxygen-free environment in the step (3) is an inert gas protected reaction environment;

the reaction temperature is 150-230° C.;

the reaction time is 2-8 h; and a molar ratio of ethyl 4'-hydroxy-3'-methoxybenzoylacetate to 2-isopentenyl-1,3,5-trihydroxybenzene is 1:2 to 3:1.

9. The preparation method according to claim 1, wherein the step (3) comprises the following steps: under inert gas protection, adding ethyl 4'-hydroxy-3'-methoxybenzoylacetate and 2-isopentenyl-1,3,5-trihydroxybenzene into a reaction vessel, stirring, heating, reacting, and then performing post-treatment on the resulting reaction liquid to obtain cannflavin B and/or isocannflavin B.

10. The preparation method according to claim 4, wherein the post-treatment comprises a quenching step; and the quenching step comprises: adding an acid to the reaction vessel to adjust pH of the mixture to 4.0-7.0.

* * * * *